United States Patent [19]

Jirousek et al.

[11] Patent Number: 6,107,327
[45] Date of Patent: Aug. 22, 2000

[54] THERAPEUTIC TREATMENT FOR HIV INFECTION

[75] Inventors: Michael R. Jirousek; Douglas Kirk Ways; Lawrence E. Stramm, all of Indianapolis, Ind.

[73] Assignee: Eli Lilly and Company, Indianapolis, Ind.

[21] Appl. No.: 08/917,033

[22] Filed: Aug. 26, 1997

Related U.S. Application Data

[60] Provisional application No. 60/024,873, Aug. 30, 1996.

[51] Int. Cl.$^7$ ................................................... A01N 43/38
[52] U.S. Cl. .............................................................. 514/411
[58] Field of Search ............................................... 514/411

[56] References Cited

U.S. PATENT DOCUMENTS

| 5,057,614 | 10/1991 | Davis et al. | 548/466 |
| 5,481,003 | 1/1996 | Gillig et al. | 548/455 |
| 5,491,242 | 2/1996 | Gillig et al. | 548/455 |
| 5,545,636 | 8/1996 | Heath et al. | 514/214 |
| 5,552,396 | 9/1996 | Heath et al. | 514/183 |
| 5,621,098 | 4/1997 | Heath et al. | 540/472 |

FOREIGN PATENT DOCUMENTS

| 0 428 105 A2 | 5/1991 | European Pat. Off. . | |
| 0 657 411 A1 | 2/1994 | European Pat. Off. ...... | C07C 43/174 |
| 0 588 762 A1 | 3/1994 | European Pat. Off. . | |
| 0 657 411 | 6/1995 | European Pat. Off. . | |
| 0 657 458 | 6/1995 | European Pat. Off. . | |
| 0 657 458 A1 | 6/1995 | European Pat. Off. . | |
| 94/14798 | 7/1994 | WIPO . | |
| 95/05824 | 2/1995 | WIPO . | |

OTHER PUBLICATIONS

Nobecli. 114 CA: 239669j, 1990.

Takahashi et al 112 CA: 69462a, 1989.

Ghosh, et al., *Nature*, 344:678–682 (1990).

Jakobovits, et al., *J. EMBO*, 9:1165–1170 (1990).

Kinter et al., J. Virology 64: 4306–4312, 1990.

Laurence, et al., *Biochem. Biophys. Res. Comm.*, 166:349–357 (1990).

Matthes et al., *Antiviral Res.*, 13:273–286 (1990).

Mosier et al., Immunology Today 15: 332–339, 1994.

Nabel, et al., *Nature*, 326:711–713 (1987).

Sodroski et al., Science 227: 171–173, 1985.

Jeffrey Lawrence et al. "Phorbol Ester–Mediated Induction of HIV–1 from a Chronically Infected Promonocyte Clone: Blockade by Protein Kinase Inhibitors and Relationship to Tat–Directed Trans–Activation" Biochemical and Biophysical Research Communications, vol. 166, No. 1, Jan. 15, 1990, pp. 349–357.

Wilkinson et al., "Isoenzyme Specificity of Bisindolylmaleimides Selective Inhibitors of Protein Kinase C," Biochem. J., vol. 294, No. 2, 335–337, 1993.

Fields, et al., "Human Immunodeficiency Virus Reduces Phosphorylation of its Cell Surface Receptor," Letters to Nature, vol. 333, No. 6170, 278–280, 1988.

Ito, et al., "Mechanism of Inhibitory Effect of Glycyrrhizin on Replication of Human Immunodeficiency Virus (HIV)," Antiviral Research, vol. 10, No. 6, 289–298, 1988.

*Primary Examiner*—Russell Travers
*Attorney, Agent, or Firm*—Paul R. Darkes

[57] ABSTRACT

A method for treating HIV infection is disclosed, particularly using the isozyme selective PKC inhibitor, (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its acid salt.

24 Claims, No Drawings

THERAPEUTIC TREATMENT FOR HIV INFECTION

This application claims the priority benefits of the U.S. Provisional application Serial No. 60/024,873 filed Aug. 30, 1996.

BACKGROUND OF THE INVENTION

1. Field of the Invention

The present invention is broadly directed to a method for inhibiting activation of latent human immunodeficiency virus (HIV). The invention is also directed to a method for inhibiting replication of HIV. The present invention is particularly directed to the use of a particular class of isozyme selective Protein Kinase C (PKC) inhibitors for treating HIV infection.

2. Description of Related Art

The HIV epidemic continues to grow at a rapid rate, and the clinical manifestations associated with this viral infection present increasingly more complex medical and socio-economic problems. Acute HIV infection leads to a period of rapid viral replication, followed by viremia that results in infection of 1% or more of circulating T lymphocytes, the primary target of the virus. Viremia is transient, however, because the cells infected with HIV are removed from circulation by an effective host immune response that results in a 10-to 100-fold decrease in the HIV-infected T cells. Unfortunately, no effective therapy yet exists for preventing viral activation after exposure. Thus, although the initial host response is effective in reducing and controlling HIV-infected cell numbers, it is not sufficient to prevent the postintegration latent or low-level-persistent (LLP) asymptomatic infections of host reservoir cells, such as circulating CD4+T lymphocytes and monocyte/macrophages. Thus, the ultimate pathogenic effects of HIV are not prevented and after induction from the latent or LLP state, acquired immune deficiency syndrome (AIDS) develops.

No cure has yet been found for HIV infection. Current treatments for HIV infection attempt to retard the progress of the disease or relieve its symptoms. Treatment in use today include certain dideoxynucleotides such as azidothymidine (AZT or zidovudine, Burroughs Wellcome), dideoxyinosine (ddI, Bristol-Myers Squibb) or dideoxycytidine (ddC, Hoffman-LaRoche). These agents can be toxic. Their applicability is limited because of the appearance in some patients of onerous, and sometimes lethal, side effects. These side effects include myelosuppression, peripheral neuropathy, and pancreatitis. In some patients, AZT has lost its effectiveness after prolonged use. While other drugs have been proposed for treatment of HIV infection, including the recent introduction of several HIV protease inhibitors, none have yet been demonstrated to be completely effective. Therefore, there remains a need in the art to develop additional therapeutic agents to treat HIV infection.

SUMMARY OF INVENTION

It is an object of the invention, therefore, to provide a method for inhibiting human immunodeficiency virus replication in an infected cell.

It is another object of the invention to provide a method for inhibiting human immunodeficiency virus activation in an infected cell.

It is still another object of the invention to provide a method for treating a mammal infected with human immunodeficiency virus.

These and other objects of the invention are provided by one or more of the embodiments described below.

One embodiment of the invention provides a method for inhibiting human immunodeficiency virus replication in an infected cell which comprises contacting the cell with a viral replication inhibiting amount of an inhibitor of the β isozyme of protein kinase C.

Another embodiment of the invention provides a method for inhibiting activation of human immunodeficiency virus in an infected cell which comprises contacting the cell with a viral activation inhibiting amount of an inhibitor of the β isozyme of protein kinase C.

Yet another embodiment of the invention, provides a method for treating a mammal infected with human immunodeficiency virus which comprises administering to the mammal a therapeutically effective amount of an inhibitor of the β isozyme of protein kinase C.

The present invention thus provides the art with the identify of compounds effective in treating HIV infection.

DETAILED DESCRIPTION OF THE INVENTION

It is a discovery of the present invention that the therapeutic use of a particular class of protein kinase C inhibitors, i.e., inhibitors of the β isozyme of protein kinase C, and especially β isozyme selective inhibitors of PKC, inhibits the activation and replication of HIV, especially such activation and replication associated with PKC signal transduction pathways. The particular class of PKC inhibitors may also inhibit HIV activation and replication which are associated with cAMP signal transduction pathways. Consequently, such compounds can be used therapeutically to treat patients infected with HIV.

The course of HIV infection is characterized by a short peak of viremia followed generally by a long, though variable, period of latent or persistent infection with no symptoms of disease. The HIV provirus is harbored in cells such as peripheral mononuclear cells and T lymphocytes. Activation of the latent HIV provirus in mononuclear cells and T lymphocytes is an important step in initiating the onset of clinical symptoms associated with the AIDS syndrome. HIV activation comprises the states of productive infection and reactivation of latent infection. HIV replication comprises the multiplying of the HIV genome during productive infection and reactivation of latent infection. Reactivation of the integrated, latent HIV genome, includes HIV replication, e.g., forming multiple transcripts of the HIV genome, HIV expression, e.g. translation of virus-specific proteins such as p24, virus assembling, as well as releasing infectious HIV particles and HIV proteins.

Applicants have shown that the compounds of the present invention can block the HIV expression, HIV-1 p24 production induced by PKC and cAMP signal transduction pathway activators. Though not wishing to be limited to any technical explanation, applicants believe that PKC affects viral activation via host cell transcription factors and viral trans-activator proteins. Induction of viral expression from the latent proviral or LLP state can be triggered by various cellular factors including mitogens, antigens, and cytokines. Virus expression depends on the activation state of the host cell and involves the activation of cellular PKC since stimulation of latently infected cells with PMA, a known activator of PKC, induces virus replication in a concentration-dependent manner (Laurence, et al., *Biochem. Biophys. Res. Comm.*, 166:349–357 (1990); Kinter, et al., *J. Virol.*, 64:4306–4312 (1990)). PKC inhibitors and cellular depletion of PKC by chronic phorbol ester treatment decrease HIV replication in chronically infected mononuclear cells induced by phorbol esters, tumor necrosis factor-alpha, IL-6 or lipopolysaccride (Kinter et al., *J. Virol*, 64:4306–4312 (1990)).

The effect of PKC on the viral genome was suggested to be mediated by modulation of host cell transcription factors, e.g., NF-κB, and of the viral trans-activator protein tat (Gosh, et al., *Nature*, 344:678–682 (1990); Jakobovits, et al., *EMBO*, 9:1165–1170 (1990)). TPA has been shown to enhance HIV-1 replication in chronically infected MOLT-4 HIV cell lines and there is evidence that this works by induction of NF-κB which binds to the enhancer region of HIV LTR (Nabel, et al., *Nature*, 326:711–713 (1987)). A specific role for the PKC-β isoform in activation of basal and mitogen stimulated HIV replication is implied by the ability of cells depleted of PKCs that are reconstituted with PKC-β to induce transcriptional activation of HIV replication (Jakobovits, et al., *EMBO*, 9:1165–1170 (1990)).

HIV tat protein increases gene expression during productive infection by up to 100-fold. There is evidence that PKC depleted cells exhibit a marked reduction in HIV-1 transactivation without any significant effect on the synthesis of tat protein. Transactivation in these PKC deficient cells can be restored by transfection with a wild type PKC expression vector (Jakobovits, et al., J. *EMBO*, 9:1165–1170 (1990)).

DNA topoisomerase II phosphorylation state and activity also correlates well with HIV production. Inhibition of the phosphorylation with PKC inhibitors (O-alkylglucerophospholipid analogues) results in reduction of HIV production (Matthes et al., *Antiviral Res.*, 13:273–286 (1990)). Furthermore, other PKC activators, OAG and bryostatin-1, induce HIV expression in chronically infected U1 cells (Kinter, et al., *J. Virol*, 64:4306–4312 (1990)).

Therefore, PKC inhibitor compounds as described in the present invention can be used therapeutically to treat HIV infection both by suppressing the viral activation and by inhibiting viral replication. The PKC inhibitor compounds may also be therapeutically effective in treatment of HIV infection by modulating PKC and/or cAMP signal transduction pathways, or by interacting with protein factors that regulate PKC and/or cAMP pathways.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,545,636, 5,481,003, 5,491,242, and 5,057,614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference. These compounds are administered in a therapeutically effective amount to a human to inhibit HIV replication infected in HIV and activation of latent HIV, or to treat HIV infection. These compounds can also be administered to patients at risk of the disease conditions mentioned above as prophylactics.

One preferred class of compounds for use in the method of the invention has the formula (I):

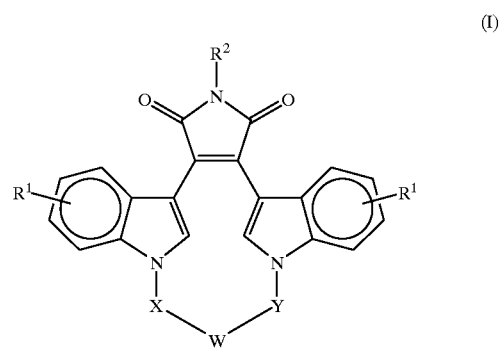

(I)

wherein:

W is —O—, —S—, —SO—, —SO$_2$—, —CO—, $C_2$–$C_6$ alkylene, substituted alkylene, $C_2$–$C_6$ alkenylene, -aryl-, -aryl(CH$_2$)$_m$O—, -heterocycle-, -heterocycle-CH$_2$)$_m$O—, -fused bicyclic, -fused bicyclic-(CH$_2$)$_m$O—, —NR$^3$—, —NOR$^3$—, —CONH—, or —NHCO—;

X and Y are independently $C_1$–$C_4$ alkylene, substituted alkylene, or together X, Y, and W combine to form —(CH$_2$)$_n$—AA—;

R$^1$s are hydrogen or up to four optional substituents independently selected from halo, $C_1$–$C_4$ alkyl, hydroxy, $C_1$–$C_4$ alkoxy, haloalkyl, nitro, —NR$^4$R$^5$, or —NHCO($C_1$–$C_4$ alkyl);

R$^2$ is hydrogen, CH$_3$CO—, —NH$_2$, or hydroxy;

R$^3$ is hydrogen, —(CH$_2$)$_m$aryl, —$C_1$–$C_4$ alkyl, —COO ($C_1$–$C_4$ alkyl), —CONR$^4$R$^5$, —(C=NH)NH$_2$, —SO ($C_1$–$C_4$ alkyl), —SO$_2$ (NR$^4$R$^5$), or —SO$_2$ ($C_1$–$C_4$ alkyl);

R$^4$ and R$^5$ are independently hydrogen, $C_1$–$C_4$ alkyl, phenyl, benzyl, or combine with the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof.

A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein R$^1$ and R$^2$ are hydrogen; and W is a substituted alkylene, —O—, S—, —CONH—, —NHCO— or —NR$^3$—. Particularly preferred compounds for use in the invention are compounds of the formula Ia:

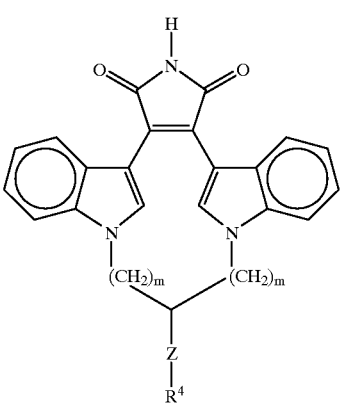

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$, or a pharmaceutically acceptable salt, prodrug or ester thereof.

Other preferred compounds for use in the method of the present invention are compounds wherein W in formula I is —O—, Y is a substituted alkylene, and X is an alkylene. These preferred compounds are represented by formula Ib:

(Ib)

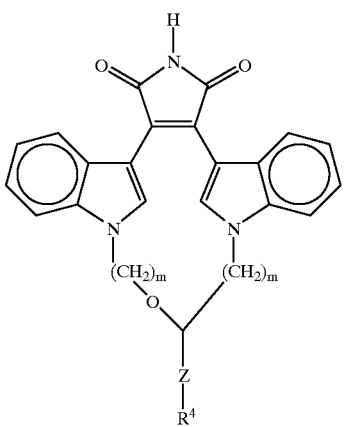

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromnide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to phatmatically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase-β inhibitor for use in the method of this invention is the compound described in Example 5 g ((S)-3,4-[N, N'-1,1'-(2"-ethoxy)-3'"(O)-4'"(N,N-dimethylamino)-butane)-bis-(3,3'-indolyl)]-

1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta -2 isozymes. Other salts of this compound also would be favored, especially the mesylate salts.

A preferred mesylate salt can be prepared by reacting a compound of the formula II

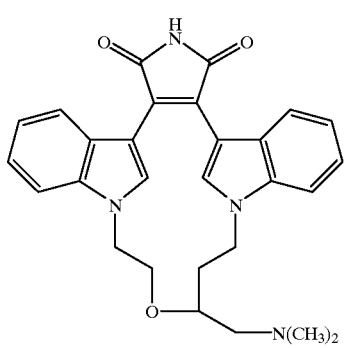

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art, directly from the reaction mixture in yields ranging from 50% to 100%. Recrystallization and other purification techniques known in the art may be used to purify the salt further if desired.

One skilled in the art will recognize that a therapeutically effective amount of the protein kinase C inhibitor of the present invention is the amount sufficient to inhibit HIV replication and/or activation or inhibit HIV effect. It is well within the ability of a person skilled in the art to measure HIV activation and replication using well known markers such as T cell count, viral count, viral specific protein, and its activity etc. The amount administered varies inter alia, depending upon the concentration of the compound in the therapeutic formulation, and the body weight of the patient. Generally, an amount of protein kinase C inhibitor to be administered as a therapeutic agent for treating HIV infection will be determined on a case by case basis by the attending physician. As a guideline, the degree of infection, the strength of the immune system, the body weight and age of the patient will be considered when setting an appropriate dose.

Generally, a suitable dose is one that results in a concentration of the protein kinase C inhibitor at the treatment site in the range of 0.5 nM to 200 µM, usually 0.5 nM to 20 µM and more usually 0.5 nM to 200 nM. It is expected that serum concentrations of 0.5 nM to 20 nM should be sufficient in most circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor should be needed. As noted above, the above amounts may vary on a case-by-case basis.

The effectiveness of the invention compounds can be tested in both in vitro and in vivo systems. For in vitro testing, chronically HIV infected mononuclear and T lymphocyte cell populations can be employed as described in Kinter et al., *J. Virology* 64: 4306–4312, 1990 and Sardoroski et al., Science 227: 171–173, 1985. Both references are incorporated herein. Results obtained from in vitro testing system are predictive of the compounds effectiveness for reducing HIV replication in the basal state as well as the compounds effectiveness for reducing HIV replication stimulated by phorbol esters, tumor necrosis factor-alpha, IL-6 and lipopolysaccride. For in vivo testing, the HIV infected humanized severe combined immunodeficiency (SCID) mouse model can be utilized (Mosier et al., Immunology Today 15: 332–339, 1994). In this model SCID mice are inoculated with HIV infected human monocytic cells or CD4+T lymphocytes. As a primary endpoint, disease progression is monitored by assessing depletion of CD4+T cells. The ability of the invention compounds to slow the decline in this model either when infected with HIV infected monocytes or CD4+T cells is predictive of a positive response in humans infected with HIV in either prolonging the latency phase or retarding the clinical progression of AIDS.

The compounds of formula I, and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 750 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon concentration of compound in the formulation. Generally, the formulation will be applied to the effected tissue in an amount affording from about 1 to about 500 $\mu$g compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The following formulation examples are illustrative only and are not intended to limit the scope of the invention in any way.

FORMULATION 1

Hard gelatin capsules are prepared using the following ingredients:

|  | Quantity (mg/capsule) |
| --- | --- |
| Active agent | 5 |
| starch, dried | 200 |
| magnesium stearate | 10 |
| Total | 215 mg |

The above ingredients are mixed and filled into hard gelatin capsules in 460 mg quantities.

FORMULATION 2

A tablet is prepared using the ingredients below:

|  | Quantity (mg/capsule) |
| --- | --- |
| Active agent | 15 |
| cellulose, microcrystalline | 10 |
| silicon dioxide, fumed | 10 |
| stearic acid | 5 |
| Total | 40 mg |

The components are blended and compressed to form tablets each weighing 665 mg.

FORMULATION 3

Tablets each containing 60 mg of active ingredient are made as follows:

|  | Quantity (mg/tablet) |
| --- | --- |
| Active agent | 6 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLES

These examples all demonstrate the use of (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione to inhibit HIV expression in U1 cells.

Example 1

In this example, the inhibitory effect of the noted compound on a PKC activator stimulated HIV expression was examined. U1 cells were treated with either PMA or PMA in combination with the noted compound. HIV expression was measured via the production of HIV-1 p24. The results as shown in Table 1 demonstrate that the noted compound has an inhibitory effect on PKC activator induced HIV expression.

TABLE 1

| Treatment | HIV-1 p24 Production (pg/ml) |
| --- | --- |
| PMA (10 µg/ml) | 3974 |
| PMA (10 µg/ml) + PKC inhibitor (1 nM) | 1899 |
| PMA (10 µg/ml) + PKC inhibitor (10 nM) | 36 |
| PMA (10 µg/ml) + PKC inhibitor (100 nM) | 1.8 |
| PMA (10 µg/ml) + PKC inhibitor (500 nM) | 9.1 |

Example 2

In this example, the inhibitory effect of the noted compound on cholera toxin stimulated HIV expression was examined. Cholera toxin is known to increase the cellular level of cAMP. U1 cells were treated with either cholera toxin or cholera toxin in combination with the noted compound. HIV expression was measured via the production of HIV-1 p24. The results as shown in Table 2 demonstrate that the noted compound has an inhibitory effect on cholera toxin induced HIV expression.

TABLE 2

| Treatment | HIV-1 p24 Production (pg/ml) |
| --- | --- |
| Cholera Toxin (CT) (10 ng/ml) | 55 |
| CT (10 µg/ml) + PKC inhibitor (1 nM) | 21 |
| CT (10 µg/ml) + PKC inhibitor (10 nM) | 10 |
| CT (10 µg/ml) + PKC inhibitor (100 nM) | 6 |
| CT (10 µg/ml) + PKC inhibitor (500 nM) | 22 |

Example 3

This example demonstrate the effects of the noted compound on TNF induced HIV expression. U1 cells were treated with either TNF or TNF in combination with the noted compound. HIV expression was measured via the production of HIV-1 p24. The results as shown in Table 3 suggest that TNF may activate HIV expression through non-PKC associated pathways.

TABLE 3

| Treatment | HIV-1 p24 Production (pg/ml) |
| --- | --- |
| TNF (10 U/ml) | 176 |
| TNF (10 U/ml) + PKC inhibitor (1 nM) | 269 |
| TNF (10 U/ml) + PKC inhibitor (10 nM) | 176 |
| TNF (10 U/ml) + PKC inhibitor (100 nM) | 185 |
| TNF (10 U/ml) + PKC inhibitor (500 nM) | 167 |

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

What is claimed is:

1. A method for inhibiting human immunodeficiency virus activation in an infected cell which comprises contacting the cell with a viral activation inhibiting amount of an inhibitor of the β isozyme of protein kinase C.

2. The method of claim 1 wherein the inhibitor of the β isozyme of protein kinase C is a bis-indolylmaleimides or a macrocyclic bis-indolylmaleimide.

3. The method of claim 1 wherein the inhibitor is isozyme selective and where the isozyme selectivity is selected from the group consisting of beta-1 and beta-2 isozymes.

4. The method of claim 3 wherein the protein kinase C inhibitor has the following formula:

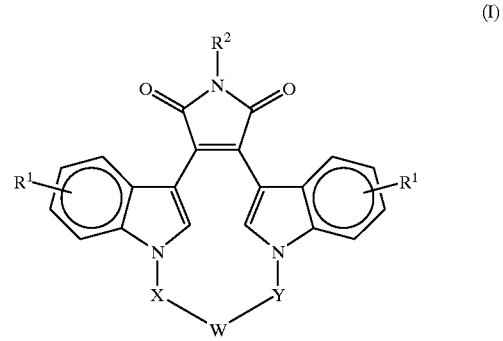

(I)

wherein:

W is —O—, —S—, —SO—, —SO$_2$—, —CO—, $C_2$–$C_6$ alkylene, substituted alkylene, $C_2$–$C_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently $C_1$–$C_4$ alkylene, substituted alkylene, or together X, Y, and W combine to form —(CH$_2$)$_n$—AA—;

R$^1$s are hydrogen or up to four optional substituents independently selected from halo, $C_1$–$C_4$ alkyl, hydroxy, $C_1$–$C_4$ alkoxy, haloalkyl, nitro, NR$^4$R$^5$, or —NHCO($C_1$–$C_4$ alkyl);

R$^2$ is hydrogen, CH$_3$CO—, NH$_2$, or hydroxy;

R$^3$ is hydrogen, (CH$_2$)$_m$aryl, $C_1$–$C_4$ alkyl, —COO($C_1$–$C_4$ alkyl), —CONR$^4$R$^5$, —(C═NH)NH$_2$, —SO($C_1$–$C_4$ alkyl), —SO$_2$(NR$^4$R$^5$), or —SO$_2$ ($C_1$–$C_4$ alkyl);

R$^4$ and R$^5$ are independently hydrogen, $C_1$–$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

5. The method of claim 4 wherein the protein kinase C inhibitor has the following formula:

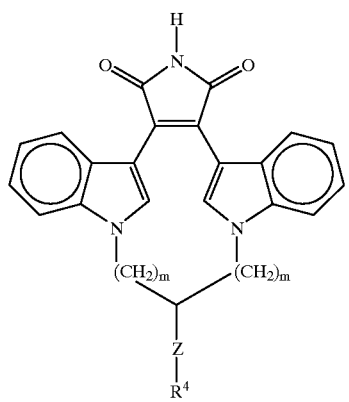

(Ia)

wherein Z is —$(CH_2)_p$— or —$(CH_2)_p$—O—$(CH_2)_p$—; $R^4$ is hydroxy, —SH, $C_1$–$C_4$ alkyl, $(CH_2)_m$aryl, —NH(aryl), —N($CH_3$) ($CF_3$), —NH($CF_3$), or —$NR^5R^6$; $R^5$ is hydrogen or $C_1$–$C_4$ alkyl; $R^6$ is hydrogen, $C_1$–$C_4$ alkyl or benzyl; p is 0, 1, or 2; and m is independently 2 or 3, or a pharmaceutically acceptable salt, prodrug or ester thereof.

6. The method of claim 4 wherein the protein kinase C inhibitor has the following formula:

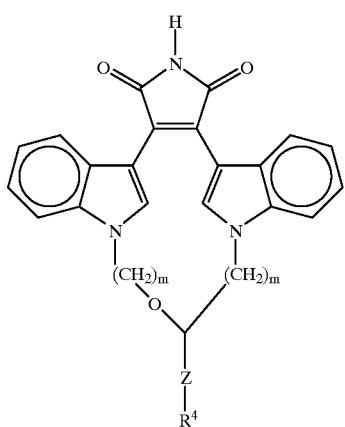

(Ib)

wherein Z is —$(CH)_p$—; $R^4$ is —$NR^5R^6$, —NH($CF_3$), or —N($CH_3$) ($CF_3$); $R^5$ and $R^6$ are independently H or $C_1$–$C_4$ alkyl; p is 0, 1, or 2; and m is independently 2 or 3, or a pharmaceutically acceptable salt, prodrug or ester thereof.

7. The method of claim 4, wherein the protein kinase C inhibitor comprises (S)-3,4-[N, N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

8. A method of claim 7, wherein the pharmaceutically acceptable acid salt is selected from the hydrochloride sale and the mesylate salt.

9. A method for inhibiting human immunodeficiency virus replication in an infected cell which comprises contacting the cell with a viral replication inhibiting amount of an inhibitor of the β isozyme of protein kinase C.

10. The method of claim 9 wherein the inhibitor of the β isozyme of protein kinase C is a bis-indolylmaleimides or a macrocyclic bis-indolylmaleimides.

11. The method of claim 9 wherein the inhibitor is isozyme selective and where the isozyme selectivity is selected from the group consisting of beta-1 and beta-2 isozymes.

12. The method of claim 11 wherein the protein kinase C inhibitor has the following formula:

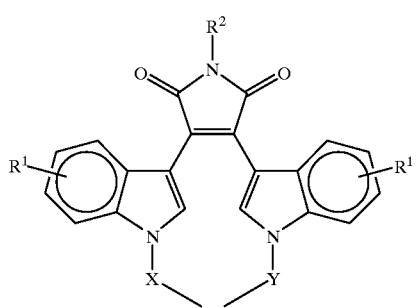

(I)

wherein:

W is —O—, —S—, —SO—, —$SO_2$—, —CO—, $C_2$–$C_6$ alkylene, substituted alkylene, $C_2$–$C_6$ alkenylene, -aryl-, -aryl$(CH_2)_m$O—, -heterocycle-, -heterocycle-$(CH_2)_m$O—, -fused bicyclic-, -fused bicyclic-$(CH_2)_m$O—, —$NR^3$—, —$NOR^3$—, —CONH—, or —NHCO—;

X and Y are independently $C_1$–$C_4$ alkylene, substituted alkylene, or together X, Y, and W combine to form —$(CH_2)_n$—AA—;

$R^1$ s are hydrogen or up to four optional substituents independently selected from halo, $C_1$–$C_4$ alkyl, hydroxy, $C_1$–$C_4$ alkoxy, haloalkyl, nitro, $NR^4R^5$, or —NHCO($C_1$–$C_4$ alkyl);

$R^2$ is hydrogen, $CH_3$CO—, $NH_2$, or hydroxy;

$R^3$ is hydrogen, $(CH_2)_m$aryl, $C_1$–$C_4$ alkyl, —COO($C_1$–$C_4$ alkyl), —$CONR^4R^5$, —(C═NH)$NH_2$, —SO($C_1$–$C_4$ alkyl), —$SO_2$ ($NR^4R^5$), or —$SO_2$ ($C_1$–$C_4$ alkyl);

$R^4$ and $R^5$ are independently hydrogen, $C_1$–$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

13. The method of claim 12 wherein the protein kinase C inhibitor has the following formula:

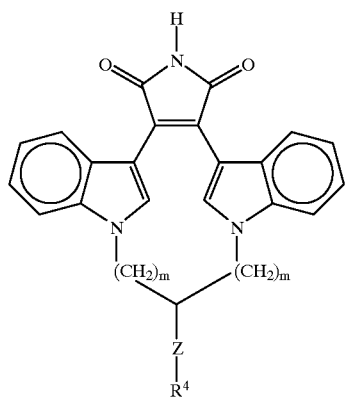

(Ia)

wherein Z is —(CH$_2$)$_p$— or —O—(CH$_2$)$_p$—; R$^4$ is hydroxy, —SH, C$_1$–C$_4$ alkyl, —(CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof.

14. The method of claim 12 wherein the protein kinase C inhibitor has the following formula:

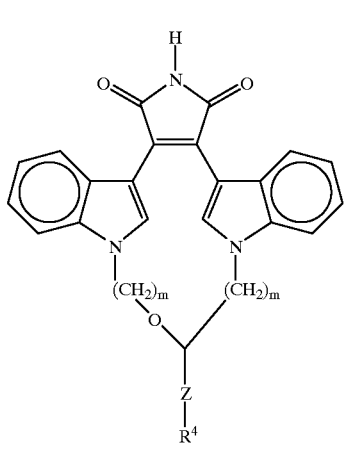

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

15. The method of claim 12, wherein the protein kinase C inhibitor comprises (S)-3,4-[N,N'-1,1'-((2"ethoxy)-3'"(O)-4'"-(N,N-dimethylamino)-butane)-bis-(3,3'-indolyl)]-1(H)-pyrrole-2,5-dione or its pharmaceutically acceptable acid salt.

16. A method of claim 15, wherein the pharmaceutically acceptable acid salt is selected from the hydrochloride salt and the mesylate salt.

17. A method for treating a mammal infected with human immunodeficiency virus which comprises administering to the mammal a therapeutically effective amount of an inhibitor of the β isozyme of protein kinase C.

18. The method of claim 17 wherein the inhibitor of the β isozyme of protein kinase C is a bis-indolylmaleimides or a macrocyclic bis-indolylmaleimides.

19. The method of claim 17 wherein the inhibitor is isozyme selective and where the isozyme selectivity is selected from the group consisting of beta-1 and beta-2 isozymes.

20. The method of claim 19 wherein the protein kinase C inhibitor has the following formula:

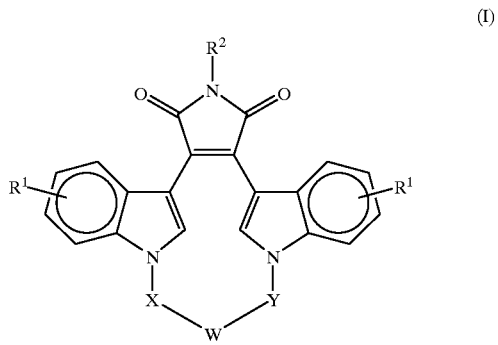

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy;

R$^3$ is hydrogen, (CH$_2$)$_m$aryl, C$_1$–C$_4$ alkyl, —COO(C$_1$–C$_4$ alkyl), —CONR$^4$R$^5$, —(C=NH)NH$_2$, —SO(C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

21. The method of claim 20 wherein the protein kinase C inhibitor has the following formula:

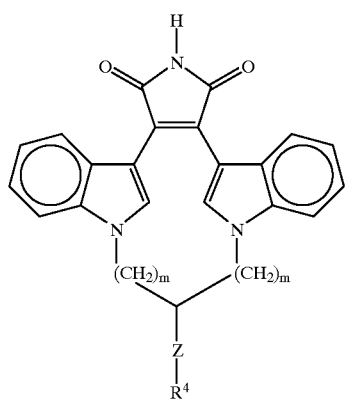

(Ia)

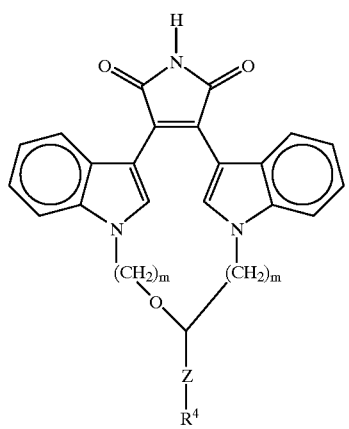

(Ib)

wherein Z is —(CH)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof.

22. The method of claim 20 wherein the protein kinase C inhibitor has the following formula:

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

23. The method of claim 20, wherein the protein kinase C inhibitor comprises (S)-3,4-[N,N'-1,1'((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

24. A method of claim 23, wherein the pharmaceutically acceptable acid salt is selected from the hydrochloride salt and the mesylate salt.

* * * * *